United States Patent
Chavanne et al.

(10) Patent No.: US 11,856,861 B2
(45) Date of Patent: Dec. 26, 2023

(54) SPRING WITH A PLURALITY OF ELEMENTS, AND ACTUATOR INCLUDING SUCH AS A SPRING

(71) Applicant: ECOLE POLYTECHNIQUE FEDERALE DE LAUSANNE (EPFL), Lausanne (CH)

(72) Inventors: Jonathan Chavanne, Lausanne (CH); Yoan Civet, Publier (FR); Yves Perriard, Neuchâtel (CH)

(73) Assignee: Ecole Polytechnique Federale De Lausanne, Lausanne (CH)

( * ) Notice: Subject to any disclaimer, the term of this patent is extended or adjusted under 35 U.S.C. 154(b) by 545 days.

(21) Appl. No.: 16/767,106

(22) PCT Filed: Nov. 23, 2018

(86) PCT No.: PCT/IB2018/059267
§ 371 (c)(1),
(2) Date: May 26, 2020

(87) PCT Pub. No.: WO2019/102417
PCT Pub. Date: May 31, 2019

(65) Prior Publication Data
US 2021/0361929 A1    Nov. 25, 2021

(30) Foreign Application Priority Data
Nov. 27, 2018   (CH) .................... 01440/17

(51) Int. Cl.
*H10N 30/88*   (2023.01)
*A61M 60/289*   (2021.01)
(Continued)

(52) U.S. Cl.
CPC .......... *H10N 30/886* (2023.02); *A61M 39/22* (2013.01); *A61M 60/117* (2021.01);
(Continued)

(58) Field of Classification Search
CPC ... H01L 41/0536; H01L 41/08; H01L 41/081; H01L 41/0825; H01L 41/0831;
(Continued)

(56) References Cited

U.S. PATENT DOCUMENTS 4,383,195 A    5/1983   Kolm et al.
6,833,656 B2 *  12/2004  Hooley ................. H01L 41/094
                                                    310/369

(Continued)

FOREIGN PATENT DOCUMENTS

WO   WO-2017/086785 A1   5/2017

OTHER PUBLICATIONS

International Search Report & Written Opinion for PCT/IB2018/059267, dated Jan. 22, 2019, 13 pages.

*Primary Examiner* — Eduardo A Rodela
(74) *Attorney, Agent, or Firm* — Blank Rome LLP

(57) ABSTRACT

A spring (3, 3') comprising a plurality of elements (30), each element (3) comprising a rigid portion (31) and a flexible beam (32), the extremities (320, 321) of the flexible beam being supported by the rigid portion (31), the flexible beam (32) having a single stable position, so that the flexible beam can be deformed when a pressure is exerted between said extremities in the direction of the rigid portion (31), and returns to said single stable position when the pressure is released, and wherein the rigid portion (31) of at least one element (30) is in contact with the flexible beam (32) of the next element between said extremities (320, 321) of the flexible beam (32), so that the spring has a negative stiffness over an operating range. The arrangement ensures a pure radial compression/expansion of the spring.

14 Claims, 9 Drawing Sheets

(51) Int. Cl.
  *A61M 60/161* (2021.01)
  *A61M 60/486* (2021.01)
  *A61M 60/839* (2021.01)
  *A61M 39/22* (2006.01)
  *A61M 60/117* (2021.01)
  *H10N 30/50* (2023.01)
  *H10N 30/857* (2023.01)

(52) U.S. Cl.
  CPC ........ *A61M 60/161* (2021.01); *A61M 60/289* (2021.01); *A61M 60/486* (2021.01); *A61M 60/839* (2021.01); *H10N 30/50* (2023.02); *F16F 2228/063* (2013.01); *H10N 30/857* (2023.02)

(58) Field of Classification Search
  CPC ............. H01L 41/0833; H01L 41/0835; H01L 41/0836; H01L 41/087; H01L 41/092; H01L 41/083; H01L 41/193; B81B 3/00; B81B 3/0013; B81B 3/0018; B81B 3/0032; B81B 3/0035; B81B 3/0062; B81B 3/0094; B81B 3/0097; B81B 5/00; B81B 2201/018; B81B 2201/036; B81B 2201/038; B81B 2203/0163; B81B 2203/0172; F16F 2228/063
  See application file for complete search history.

(56) References Cited

U.S. PATENT DOCUMENTS

| | | | |
|---|---|---|---|
| 7,064,472 B2 | 6/2006 | Pelrine et al. | |
| 7,128,707 B2 | 10/2006 | Banik | |
| 7,371,223 B2 | 5/2008 | Couvillon, Jr. et al. | |
| 7,411,331 B2 | 8/2008 | Dubowsky et al. | |
| 8,016,739 B2 | 9/2011 | Peters et al. | |
| 9,121,507 B2* | 9/2015 | Ghalambor | F16J 15/3452 |
| 2004/0183632 A1* | 9/2004 | Howell | B81B 3/0054 |
| | | | 335/78 |
| 2008/0157631 A1 | 7/2008 | Heim et al. | |
| 2013/0096887 A1* | 4/2013 | Fee | F16F 1/3605 |
| | | | 267/153 |
| 2016/0144091 A1 | 5/2016 | Breedon et al. | |
| 2017/0055903 A1* | 3/2017 | Cramer | A61B 5/6843 |
| 2018/0128336 A1* | 5/2018 | Bullard | F16F 1/18 |
| 2019/0044052 A1* | 2/2019 | Zelka | H01L 41/253 |

* cited by examiner

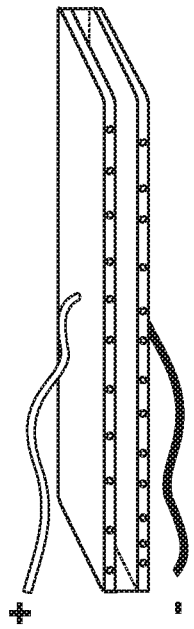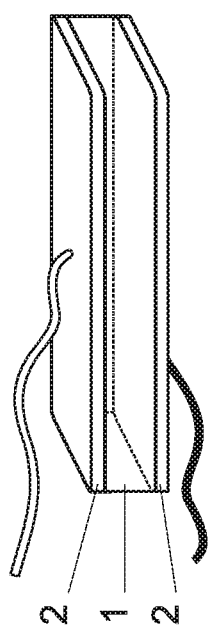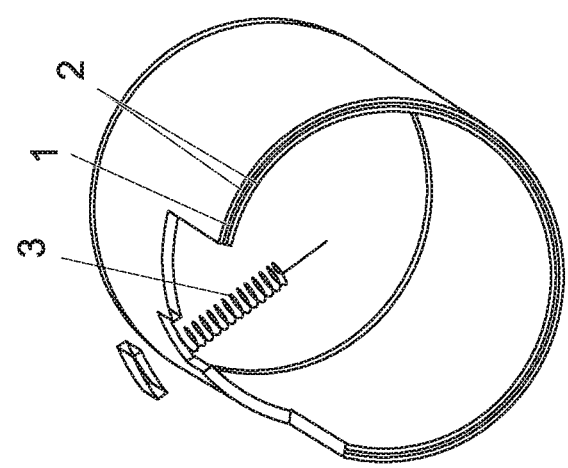

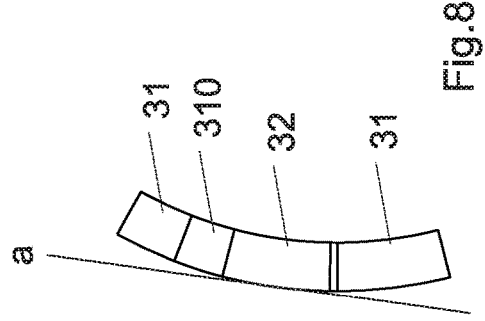
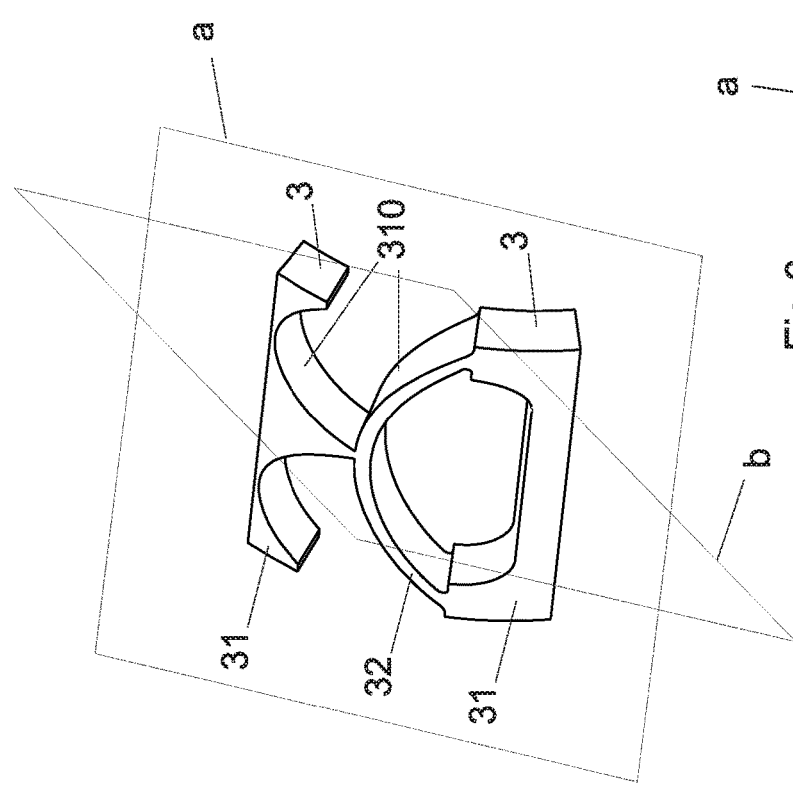
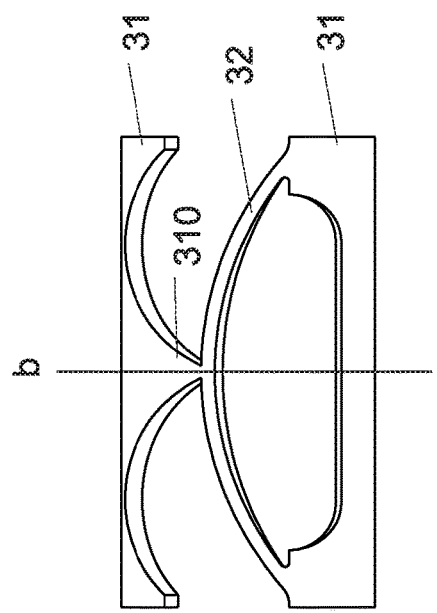
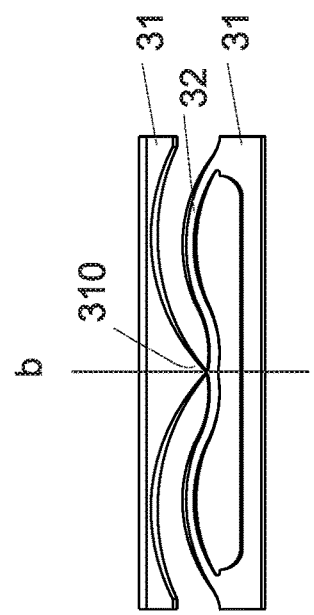

SPRING WITH A PLURALITY OF ELEMENTS, AND ACTUATOR INCLUDING SUCH AS A SPRING

RELATED APPLICATIONS

This application is a national phase of PCT/IB2018/059267, filed on Nov. 23, 2018, which claims the benefit of Swiss Application No. CH014410/17, filed on Nov. 27, 2017. The entire contents of these applications are hereby incorporated by reference.

FIELD OF THE INVENTION

The present invention concerns a spring comprising a plurality of elements, and an actuator comprising an electroactive polymer and such a spring.

Such an actuator could be used for example as an organ compression device, such as an aortic compression device or artificial sphincter.

DESCRIPTION OF RELATED ART

Cardiovascular disease generally refers to conditions that involve narrowed or blocked blood vessels, or other heart conditions, that can lead to a heart attack, chest pain (angina) or stroke. If the damage to the muscle is severe, invasive surgery may be necessary, which can involve the implantation of a heart assistance device.

An aortic compression device has been described in US8016739 to increase coronary blood flow. The device alternately compresses and decompresses the aorta of the heart to be assisted. It comprises a pump adapted to pump the fluid from a reservoir within the chest of the patient to the compression device. Implanting a pump, a compression device and a fluid reservoir within the body of a patient is difficult.

A pump that requires less components has been described in US7064472. As schematically illustrated on FIG. 1A, this document suggests an electroactive polymer film 1 whose dimensions are controlled by applying a voltage to electrodes 2 on each side of the film. The reduction in thickness, illustrated on FIG. 1B is used to pump a liquid.

Pumps based on electroactive polymers are compact and reliable, and therefore well adapted to the control of fluid displacement within a living body. U.S. Pat. No. 7,128,707 discloses an artificial sphincter based on such an electroactive polymer. U.S. Pat. No. 7,371,223 discloses an electroactive polymer actuated heart-lung bypass pump.

U.S. Pat. No. 7,411,331 discloses another actuator comprising an elastomeric film coated on both surfaces with electrodes. The system is actuated by applying a voltage to the electrodes, which causes the film to compress in thickness and expand in surface area. In order to avoid high voltages that would be necessary in order to achieve great pressure, the document suggests pre-stretching the dielectric material.

A mechanical equivalent of such an actuator comprising an electroactive polymer film 1,2 and a spring 3 is schematically illustrated on FIG. 2. In this example, the film has a cylinder form and the pre-stretching spring 3 acts against the surface of the film. The diameter of the cylinder depends on the voltage applied to the electrodes 2 on the inner and outer surface of the film, and on the stiffness of the spring 3.

The force generated by such an electrostatic actuator 1,2, 3 whose stiffness is positive is not constant throughout the stroke; rather, it reaches its maximum at the beginning (with no voltage applied) and decreases linearly when a voltage is applied, until the end of the stroke. This situation is schematically represented on FIG. 3A.

An actuator that provides a more uniform force could be desirable. In order to achieve this target, U.S. Pat. No. 7,411,331 suggests compensating the positive stiffness of the electroactive polymer film 1 with a spring having a constant and negative stiffness over a certain range, as illustrated on FIG. 3B. Coupling an electroactive polymer film with a pre-constrained spring having a negative stiffness increases the amount of displacement that can be achieved with a given voltage or energy.

By carefully designing the spring, the combined actuator can be tuned to have zero stiffness and constant force output over the operative range of displacement, as illustrated on FIG. 3C.

The spring suggested in U.S. Pat. No. 7,411,331 comprises a bi-stable element with a base that supports two opposing flexure arms. The device has two stable configurations; between these bi-stable states, there is an area where the force-displacement curve is approximately linear and has a negative slope.

A problem of this design is that the range over which the force-displacement curve of the bi-stable device is linear with a negative slope is limited, to avoid two stable positions. Therefore, the operating range and maximal displacement of the device is limited, making it barely suitable when a higher range of operation with high efficiency is required, such as in an aortic pump.

US2008/157631 discloses a transducer having an electrostatic polymer actuator that is biased with a negative rate spring, The operating range over which a negative force-displacement factor applies is limited.

It is therefore an aim of the invention to provide a spring that could be used in such an electrostatic polymer actuator, and which has a negative force-displacement factor over a wider operating range.

Another aim of the invention is to build a spring with a purely radial deformation.

BRIEF SUMMARY OF THE INVENTION

According to the invention, these aims are achieved by means of a spring comprising a plurality of elements, each element comprising a rigid portion and a flexible beam, the extremities of the beam being supported by the rigid portion, the flexible beam having a single stable position, so that the flexible beam can be deformed when a pressure is exerted between said extremities in the direction of the rigid portion, and returns from itself to said single stable position when the pressure is released, and wherein the rigid portion of at least one element is in contact with the flexible beam of the next element between said extremities of the flexible beam so that the spring has a negative stiffness over an operating range.

A beam with a single stable position is a beam which is shaped and/or mounted so that it returns to a single, normal, stable position when no additional external forces are applied.

Tests and simulations have shown that the use of springs with such a monostable flexible beam provides a negative force-displacement factor over a larger range than known solutions based on bi-stable springs. They are, therefore, more suitable to obtain a larger displacement.

It is, therefore, possible to control the stiffness of the electroactive film, and thus to increase the for a given actuator.

Pseudo-monostable springs exist that are based on bi-stable springs and abutments to limit the displacements around one of the two stable positions. However, those abutments further limit the range of displacement, and thus the stroke. Moreover, the shock (or impact) against the spring and the abutments results in energy being wasted, and reduced durability.

Therefore, in the inventive device, the displacements of the monostable spring are not limited by any external abutment, and the spring is truly monostable over the whole linear range, and over the whole operational range.

In one embodiment, the flexible beam is curved between its two extremities, like a bow. Its stable position corresponds to a given curvature. The radius of the curve is reduced when the pressure is exerted, or at least one additional inflection point is added to the beam.

The flexible beam may be curved in two planes.

The rigid portion may comprise a prominent extension connected to the flexible beam of the adjacent element, between the two extremities of this flexible beam.

In one embodiment, the rigid portion is connected to the center of the flexible beam of the adjacent element.

The spring may be formed as a ring with N said elements. The flexible beam of the first element may be in contact with the rigid portion of the Nth element, so that the diameter of the ring is reduced when each rigid portion exerts a pressure on the flexible beam of the next element.

The spring may comprise a plurality of rows of elements, so that the rigid portion of each element is integrally connected with the rigid portion of another element in an adjacent row.

The spring may comprise an even number of such rows.

This arrangement ensures a pure radial compression/expansion.

The adjacent elements of the spring may be oriented head-to-tail, so that the flexible beam of the elements in one row are connected to the rigid support of the next element, while the flexible beam of the elements in one row are connected to the rigid supports of the previous element.

In other embodiments, the adjacent elements of the spring might be connected head-to-head or tail-to-tail or in such way to remove any unwished force and/or displacement component(s).

The invention is also related to an actuator comprising at least one layer of electroactive polymer and a spring as described, for pre-stretching the electroactive polymer.

In one embodiment, this actuator is used for an implantable ventricular assist device.

In one embodiment, this actuator is used for an artificial sphincter.

BRIEF DESCRIPTION OF THE DRAWINGS

The invention will be better understood with the aid of the description of an embodiment given by way of example and illustrated by the figures, in which:

FIG. 1A shows an electroactive polymer film with one electrode on each side;

FIG. 1b shows an electroactive polymer film with one electrode on each side, a voltage being applied between the electrodes;

FIG. 2 shows a cylindrical actuator comprising an electroactive polymer film with electrode on the inner and outer surface of the cylinder, and a pre-stretching/return spring;

FIG. 6 is a perspective view of two different portions of two consecutive elements of a spring according to the first embodiment of the invention;

FIG. 7A is a side view of two different portions of two consecutive elements of a spring according to the first embodiment of the invention, in uncompressed state;

FIG. 7B is a side view of two different portions of two consecutive elements of a spring according to the first embodiment of the invention, in compressed state;

FIG. 8 is a lateral view of two different portions of two consecutive elements of a spring according to the first embodiment of the invention;

DETAILED DESCRIPTION OF POSSIBLE EMBODIMENTS OF THE INVENTION

The already described FIG. 1A schematically illustrates a film comprising an electroactive polymer 1 between two conductive electrodes 2. The thickness of the film is reduced, and its size is increased, when a voltage is applied between the two electrodes, as shown on FIG. 1B.

FIG. 2 schematically represents a cylindrical actuator comprising the electroactive polymer film of FIG. 1A, 1B. The electroactive film 1 is rolled as a cylinder and the electrodes 2 are provided on the inside and on the outer surface of this cylinder. The application of a voltage between those two electrodes increases the diameter of the cylinder. A pre-stretching spring, schematically represented as 3 on the figure, insures the expansion of the diameter of the cylinder.

Figure 3C:
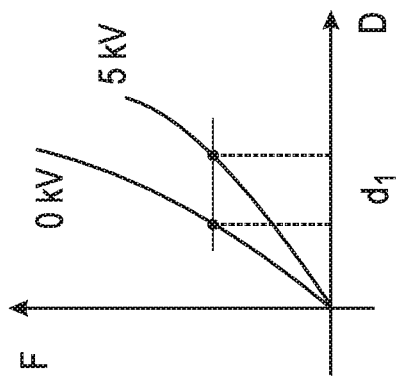
FIG. 3C is a diagram of the force to displacement relationship of a constant-force load with an electroactive film.
Figure 3B:
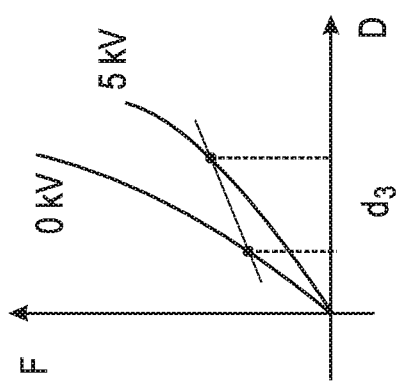
FIG. 3B is a diagram of the force to displacement relationship of a negative-stiffness spring with an electroactive film.
Figure 3A:
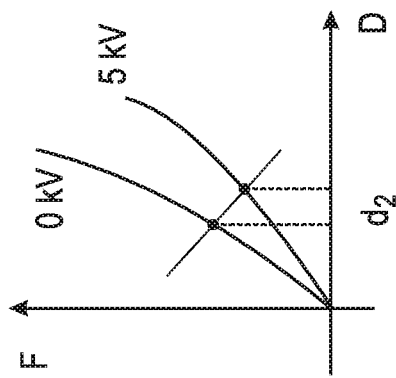
FIG. 3A is a diagram of the force to displacement relationship of a positive-stiffness spring coupled with an electroactive film.
Figure 4:
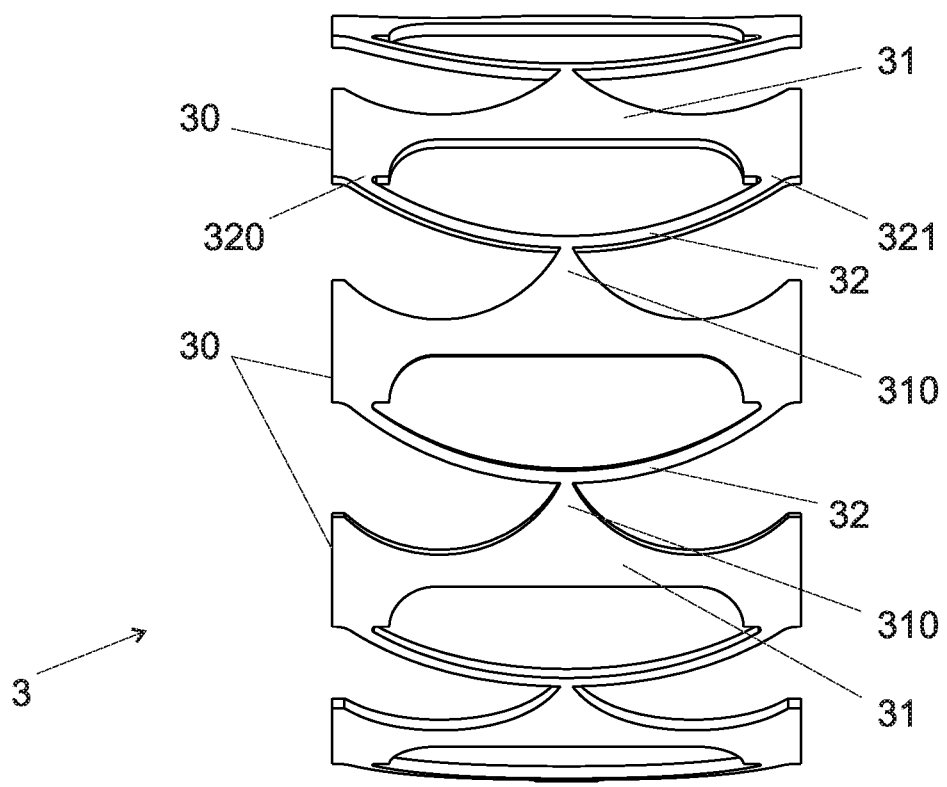
FIG. 4 is a side view of a portion of spring according to a first embodiment of the invention.
Figure 5:
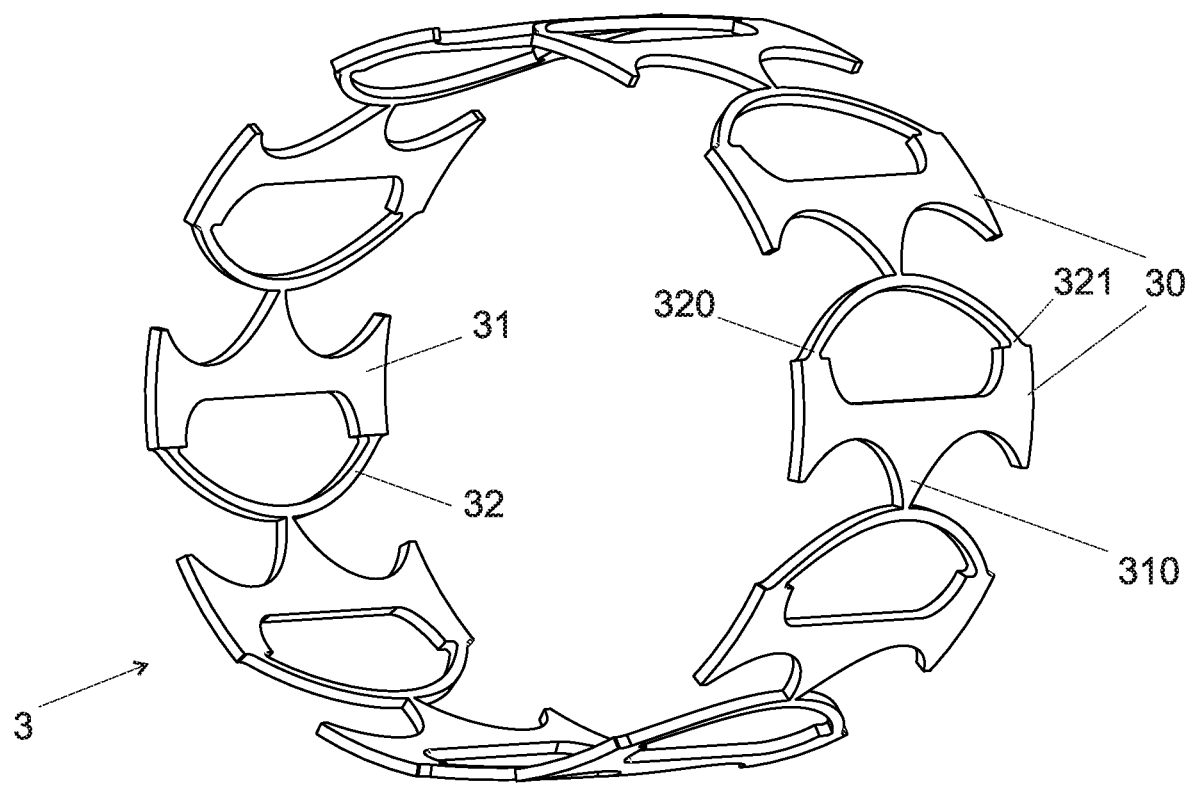
FIG. 5 is a perspective view of a spring according to the first embodiment of the invention.

FIG. 3A illustrates the relationship between the displacement D (variation of radius of the cylindrical actuator) and the force exerted by the film 1, for two values of the voltage applied between the electrodes 2. In this figure, the electroactive film 1 is coupled with a pre-constrained spring 3 having a positive stiffness. The displacement achieved when the voltage between is increased, for example from 0 kV to 5 kV, is indicated with dz. As one can see, the force at the equilibrium position exerted by the system 1, 2, 3 decreases when the voltage applied between the electrodes increases.

FIG. 3B illustrates the relationship between the displacement D (variation of radius of the cylindrical actuator) and the force exerted by the film 1, for two values of the voltage applied between the electrodes 2. In this figure, the electroactive film 1 is coupled with a pre-constrained spring 3 having a negative stiffness, so that the force exerted by the spring 3 helps for the displacement. Therefore, the value of the displacement $d_3$ obtained for a given increase of the voltage is larger than the value $d_2$ that was achieved in the case of FIG. 3A when a spring with a positive stiffness is used. Moreover, the force at the equilibrium position exerted by the system 1, 2, 3 increases with the voltage.

FIG. 3C illustrates a relationship where the resulting compression force is constant over the whole displacement range of the electroactive film, over the whole operation range, for example independently of the diameter. An actuator with a constant force can be designed by compensating the stiffness of the electroactive film with a pre-stretching spring of opposite stiffness, as will be described.

FIG. 4-8 illustrates a first embodiment of a cylindrical spring 3 having a negative and constant stiffness over its operative range, i.e. a positive and linear relationship between its variation in diameter and the applied force, as shown on FIG. 3A. Such a spring 3 could be used for pre-stretching this film.

The spring 3 comprises a plurality N of mutually connected elements 30. Each element comprises a rigid portion 30 and a flexible beam 32. The extremities 320, 321 of the beam 32 are supported by the rigid portion 31, so that the beam 32 is curved (like a bow) between those two extremities. Each beam 32 can comprise one single element, or a plurality of parallel mounted elements.

The transversal section of the flexible beam 32 has preferably a constant surface over the whole length of the beam. This surface is preferably much smaller than the surface of any transversal section of the rigid portion. The thickness of each element is preferably constant, to facilitate manufacturing. Beams of variable sections, and spring elements of variable thickness, could also be considered.

Each flexible beam 32 has one single stable position, so that it will resist any deviation from this stable position.

A pressure between the extremities 320, 321 of the beam in the direction of the rigid portion will result in a deformation of the beam. The deformation might consist in a deformation of the beam, so that the radius of curvature of the beam 32 is increased when a pressure is exerted. Alternatively, or when the pressure is more important, at least one additional point of inflection will be added between the two extremities, as shown on FIG. 7B. The flexible beam 32 elastically returns to its single stable position when the pressure is released. The rigid portions of adjacent elements remain parallel during the whole compression.

Each rigid portion 31 is in contact with the flexible beam 32 of the next element between the extremities of the flexible beam. In the illustrated preferred embodiment, each rigid portion 31 comprises a prominent extension 310 in contact with the flexible beam of the next element, preferably in the center of the flexible beam 31 between its two extremities 320, 321.

The diameter of the cylindrical spring 3 is reduced when each rigid portion 31 exerts a pressure on the next flexible beam 32, resulting in a deformation of this beam.

The number N of elements 30 in the spring 3 depends on the desired diameter, and on the variation of diameter that needs to be achieved. This number N is preferably even to ensure a higher symmetry. In one embodiment, the number N of elements is comprised between 8 and 50, preferably between 8 and 16.

The spring could be made of any elastic material, such as polymer, silicon, and/or metal. In one embodiment suitable for implantable medical devices, it is made of Titanium.

All the elements 30 of one spring 3 are preferably monolithic, without any assembly. The spring can be fabricated by additive manufacturing (such as 3D printing), photolithography, and/or electrical discharge machining (EDM).

FIG. 6 is a perspective view of two different sub-portions of two consecutive elements 30 of a spring 3. As shown on FIG. 7, the flexible beam 32 of each element is curved in a first plane a, tangential to the cylindrical spring and in which the deformation of the beam 32 occurs. As shown on FIG. 8, the flexible beam 32 and the whole element 30 are also curved in a second plane b, perpendicular to a and transversal to the cylinder. This shape insures a continuous contact between each portion of the beams 32 and the electroactive film 1,2.

FIG. 7A is a side view of two different portions of two consecutive elements of a spring according to the first embodiment of the invention, at rest state. FIG. 7B shows the same portions in compressed state, when the latter is constrained and associated (or under operation) to the electroactive film.

Figure 9:
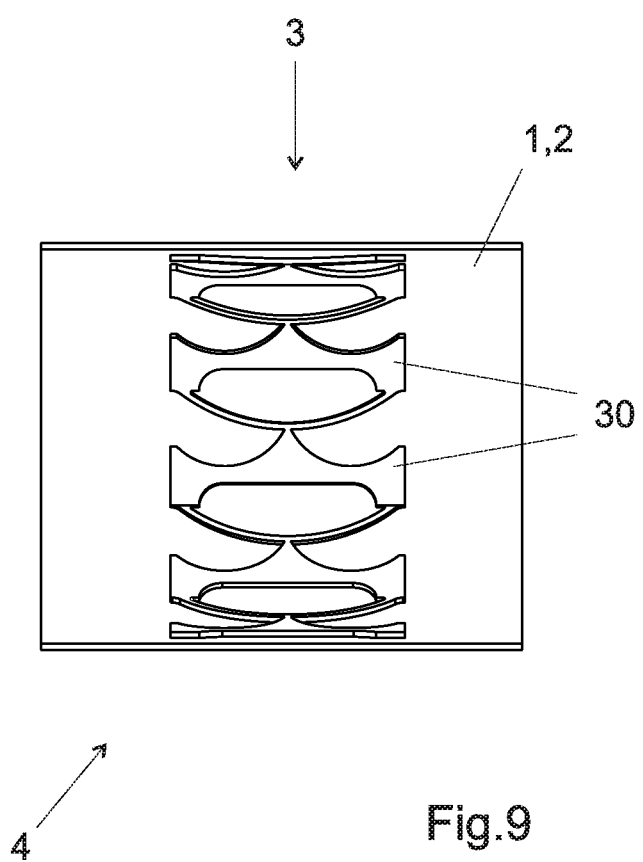
FIG. 9 is a side view of a portion of actuator with a spring according to the first embodiment of the invention.

FIG. 8 is a lateral view of two different portions of two consecutive elements of a spring according to the first embodiment of the invention;

FIG. 9 illustrates a complete actuator 4 including a cylinder of electroactive polymer film 2 with electrodes on the inner and on the outer surfaces, and a spring 3 exerting a pre-stretching force on the side of the actuator. The spring 3 is preferably positioned against the inner walls of the cylinder 1, 2; in another embodiment, it could be positioned around the outer side of this cylinder, or between two layers of a multilayer film.

Figure 10:
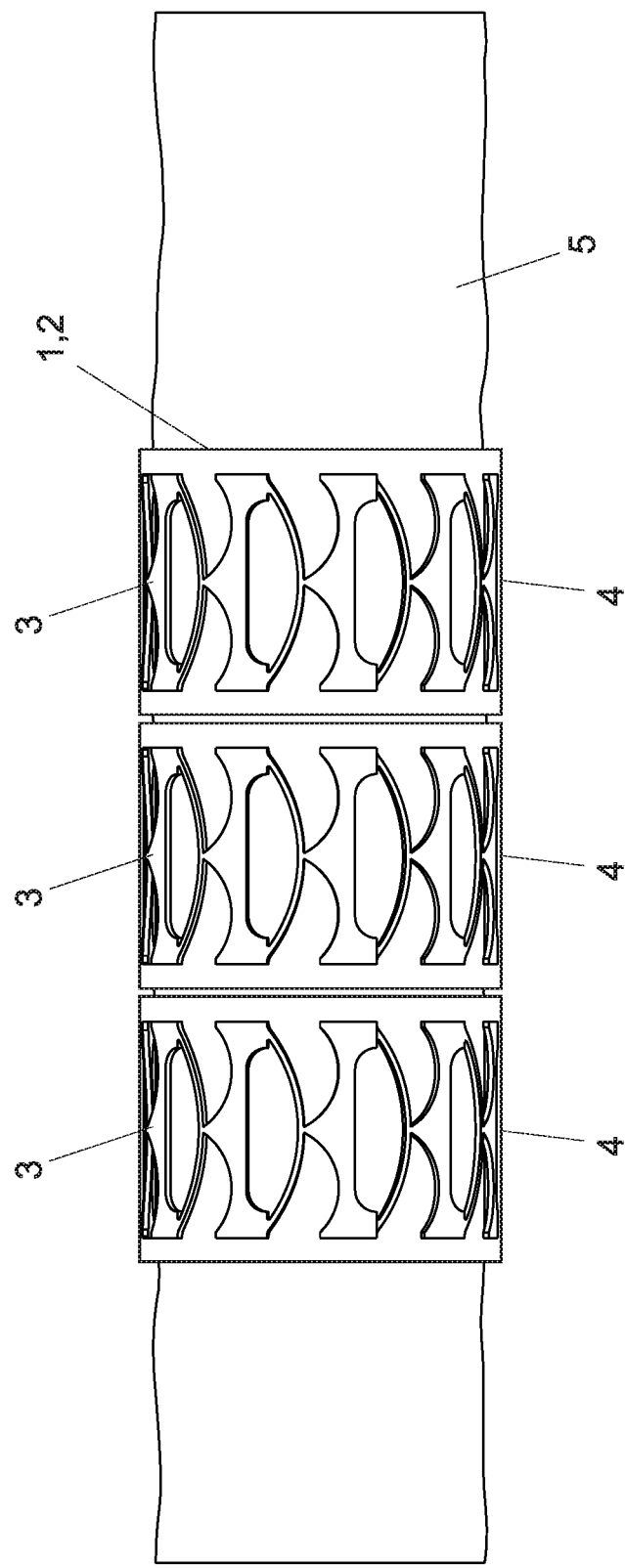
FIG. 10 is a side view of a portion of actuator with three springs according to the first embodiment of the invention, used in a peristaltic pump.

FIG. 10 shows a peristaltic pumping device comprising M actuators 4 according to FIG. 9, for example three actuators. The actuators 4 are mounted adjacent around a vessel 5, such as an aortic vessel. By controlling the expansion/compression of each actuator, a fluid inside the vessel 5 could be pumped, or at least the displacement of a liquid within that vessel could be assisted. The cylindrical electroactive film 1,2 is preferably around the spring 3. An elastic protective film could be provided between the spring 3 and the vessel 5.

Figure 11:
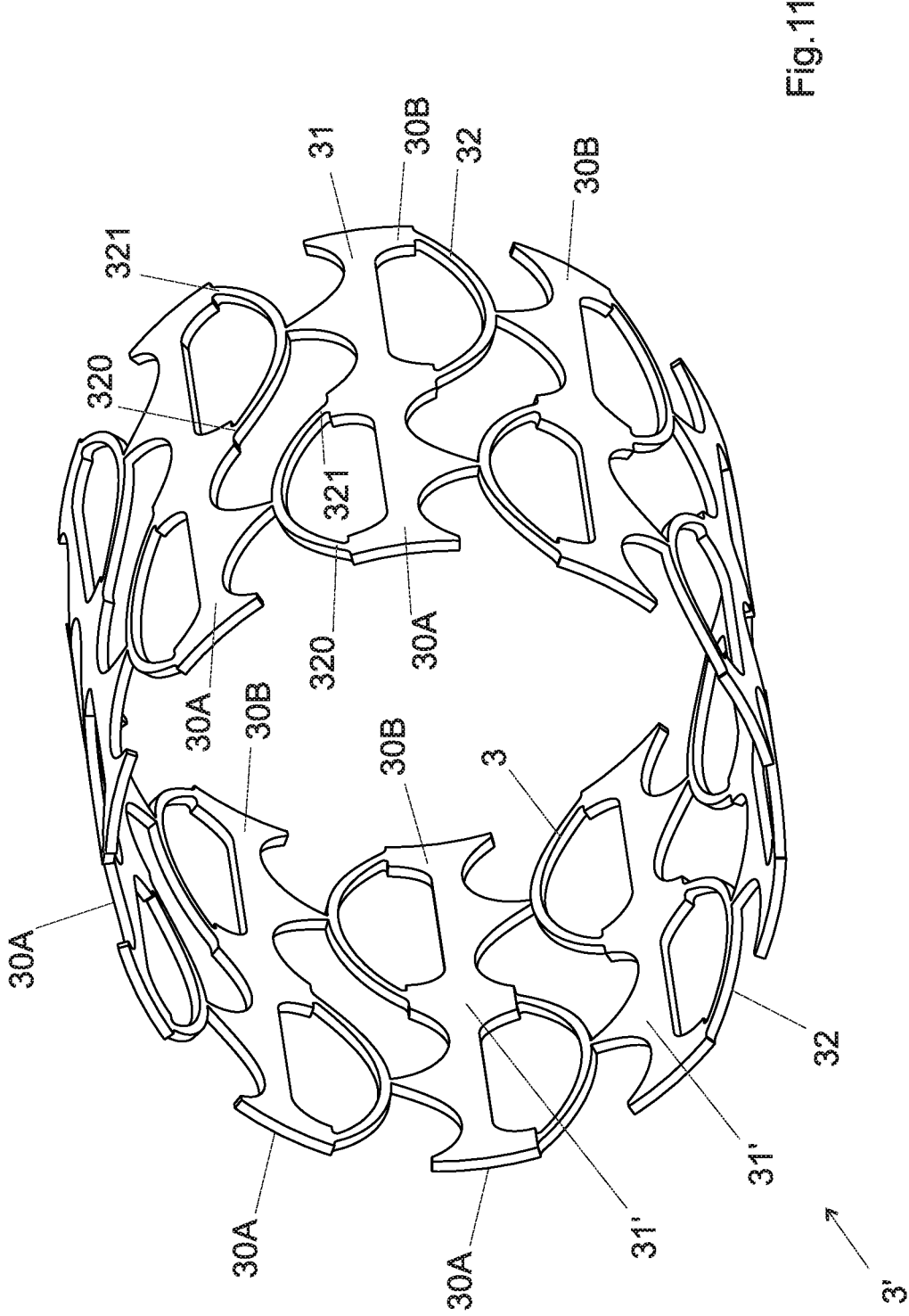
FIG. 11 is a perspective view of a spring according to a second embodiment of the invention.
Figure 12:
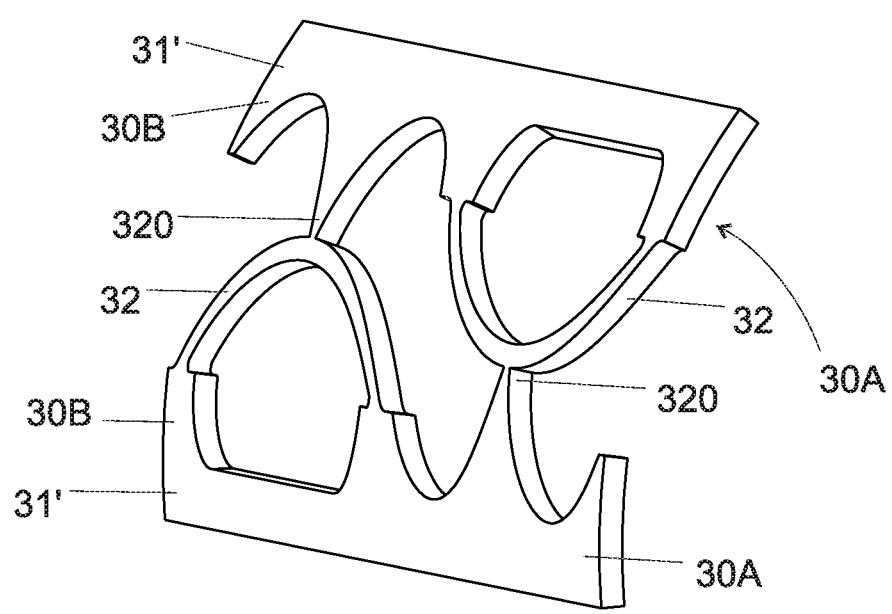
FIG. 12 is a perspective view of two different portions of two consecutive elements of a spring according to the second embodiment of the invention.

We will now describe in relation with FIGS. 11 and 12a spring 3' and an actuator according to a second and preferred embodiment of the invention. Identical reference numbers designate identical or similar or functionally identical structures or elements, and will only be repeated when needed.

In this embodiment, the spring 3' comprises a plurality (here two) of rows of spring elements 30A, 30B. The rigid portion 31' of each element is integrally connected with the rigid portion of another element in an adjacent row.

The elements 30A, 30B in adjacent rows are oriented head-to-tail, so that the flexible beams 32 of the elements 30A in one row are connected to the rigid support of the next element 30A, while the flexible beams 32 of the elements 30B in one row are connected to the rigid supports of the previous element 30B. The elements are thus disposed in an anti-symmetric way.

The number of rows is preferably even. The illustrated example comprises two rows. This arrangement, with the same number of elements pointing in one direction as the number of rows pointing in the opposite direction, insures a pure radial deformation of the spring 3' when a force is applied by the electroactive polymer, without any rotation of the elements. As in the first embodiment, the relationship between force and displacement is linear and positive over the whole operational range.

The actuator 1,2,3 (or 1,2,3') of the invention could be used as a peristaltic pump, for pumping a liquid in a tube through the actuator. Such an actuator could be used for an aortic compression device to assist the heart. The actuator could be implanted in a human body, and powered through inductive transmission through the body.

This actuator could also be used as a valve or sphincter to control transmission of a fluid with a human tube, and to block completely or authorize transmission of the fluid.

The actuator could also be planar, with a spring comprising elements 30 in a plane instead of being closed as a cylinder. Such a planar actuator could be used as a muscle, for example under the skin.

The invention claimed is:

1. An actuator comprising an annular spring and an annular electroactive polymer layer laminated to said spring in a radial configuration, said spring comprising a plurality of elements, each element comprising a rigid portion and a flexible beam, the extremities of the flexible beam being supported directly by the rigid portion, and electrodes operating the electroactive polymer layer, the flexible beam having a single stable position, so that the flexible beam can be deformed when a pressure is exerted between said extremities in the direction of the rigid portion, and returns to said single stable position when the pressure is released, so that the spring and electroactive film combination has a negative stiffness over an operating range, wherein the rigid portion of at least one element is in contact with the flexible beam of the next element between said extremities of the flexible beam.

2. Actuator according to claim 1. said flexible beam being curved between its two extremities.

3. Actuator according to claim 2, said flexible beam being curved in two planes.

4. Actuator according to claim 1, said rigid portion comprising a prominent extension connected to the center of said flexible beam of the next element.

5. Actuator according to claim 1, formed as a cylinder with N said elements, the flexible beam of the first element being in contact with the rigid portion of the Nth element, so that the diameter of said cylinder is reduced when each rigid portion exerts a pressure on the flexible beam of the next element.

6. Actuator according to claim 1, comprising a plurality of rows of said elements, so that each the rigid portion of each element in one row is integrally connected with the rigid portion of another element in an adjacent row.

7. Actuator according to claim 6, comprising an even number of rows.

8. Actuator according to claim 6, adjacent elements being oriented head-to-tail, so that the flexible beams of the elements in one row are connected to the rigid support of the next element, while the flexible beams of the elements in another row are connected to the rigid supports of the previous element.

9. Actuator according to claim 1, arranged to ensure a pure radial compression/expansion.

10. Actuator according to claim 1, said electroactive polymer being arranged for pre-stretching the electroactive polymer.

11. An implantable ventricular assist device comprising an actuator according to claim 10.

12. A sphincter comprising an actuator according to claim 10.

13. Actuator according to claim 1 wherein when a pressure is exerted between said extremities in the direction of the rigid portion the flexible beam is deformed so that the radius of curvature of the flexible beam is increased.

14. Actuator according to claim 1, further comprising a voltage source applied to the electrodes to change a size of the electroactive polymer layer.

* * * * *